United States Patent
Wells (10) Patent No.: US 6,936,012 B2
(45) Date of Patent: Aug. 30, 2005

(54) METHOD AND APPARATUS FOR IDENTIFYING CONSTITUENT SIGNAL COMPONENTS FROM A PLURALITY OF EVOKED PHYSIOLOGICAL COMPOSITE SIGNALS

(75) Inventor: Martin D. Wells, Needham, MA (US)

(73) Assignee: NeuroMetrix, Inc., Waltham, MA (US)

( * ) Notice: Subject to any disclaimer, the term of this patent is extended or adjusted under 35 U.S.C. 154(b) by 296 days.

(21) Appl. No.: 10/174,153

(22) Filed: Jun. 18, 2002

(65) Prior Publication Data

US 2003/0032889 A1 Feb. 13, 2003

Related U.S. Application Data

(60) Provisional application No. 60/298,831, filed on Jun. 18, 2001.

(51) Int. Cl.$^7$ ................................. A61B 5/05

(52) U.S. Cl. ..................................... 600/554

(58) Field of Search .................. 600/554, 300, 600/547, 544; 367/134; 702/19; 455/501; 708/109

(56) References Cited

U.S. PATENT DOCUMENTS

| 5,383,164 A | * | 1/1995 | Sejnowski et al. .......... 367/134 |
| 6,544,170 B1 | * | 4/2003 | Kajihara et al. ............ 600/300 |
| 2003/0093006 A1 | * | 5/2003 | Wells et al. ................. 600/547 |
| 2004/0111220 A1 | * | 6/2004 | Ochs et al. ................... 702/19 |

FOREIGN PATENT DOCUMENTS

| WO | WO 200213906 A1 | * | 2/2002 | ............ A61N/1/18 |

* cited by examiner

*Primary Examiner*—Max F. Hindenburg
*Assistant Examiner*—Brian Szmal
(74) *Attorney, Agent, or Firm*—Pandiscio & Pandiscio (57) ABSTRACT

A novel application of independent component analysis (ICA) to data acquired by a single sensor. The technique exploits the unique relationship between multiple physiologic (source) and electronic (artifact) components in surface recorded sensory nerve action potential (SNAP) waveforms that are evoked by different activating magnitudes. A forward model of the SNAP is developed and used to test the approach on a simplified data simulation. The method is applied to experimental data and shown to be effective at separating artifact and source components and reconstructing artifact-free traces. A method of automated reconstruction for use within an expert system is also disclosed.

49 Claims, 5 Drawing Sheets

FIG. 1

Forward model of compound sensory nerve action potential and stimulus artifact signal generation. See text for description.

FIG. 2

Results of Independent Component Estimation on simulated data before and after the addition of corrupting noise.

FIG. 3

Single channel independent component analysis applied to peripheral nerveaction potential signals. See text for description.

FIG. 4

Automated independent component analysis, source and artifact classification, and reconstruction. See text for detailed description.

FIG. 5

METHOD AND APPARATUS FOR IDENTIFYING CONSTITUENT SIGNAL COMPONENTS FROM A PLURALITY OF EVOKED PHYSIOLOGICAL COMPOSITE SIGNALS

REFERENCE TO PENDING PRIOR PATENT APPLICATION

This patent application claims benefit of prior U.S. Provisional Patent Application Ser. No. 60/298,831, filed Jun. 18, 2001 by Martin D. Wells for METHODS FOR EXTRACTING OR SEPARATING MULTIPLE EVOKED PHYSIOLOGICAL SIGNAL COMPONENTS FROM RECORDINGS CONSISTING OF THEIR MIXTURES, which patent application is hereby incorporated herein by reference.

FIELD OF THE INVENTION

This invention relates to medical apparatus and methods in general, and more particularly to methods and apparatus for identifying constituent signal components from a plurality of evoked physiological composite signals.

BACKGROUND OF THE INVENTION

Non-invasive peripheral nerve conduction studies (NCS) are an important tool in the diagnosis and assessment of neuromuscular injuries and pathologies. Electrical stimulation of a nerve bundle by surface electrodes produces impulses that travel in both the proximal and distal directions. Compound signals can be differentially recorded from the muscle or muscle group that is innervated by the stimulated nerve or from a separate location over the nerve itself. The amplitude and latency (or conduction velocity) of these evoked potential (EP) signals are calculated and used clinically to determine the location of nerve lesions and/or to provide an overall characterization of nerve function. More elaborate analysis of both compound muscle action potentials (CMAPs) and sensory nerve action potentials (SNAPs) have also been investigated and are believed to provide more precise diagnoses and assessment by extracting additional information from the complex signals.

Large artifacts due to the electrical stimuli often appear in surface EP traces. Stimulus artifacts can be significant enough in magnitude and duration to contaminate the CMAP or SNAP waveform. Signal contamination can be severe, particularly in SNAP recordings where the evoked potential may only be a few microvolts in amplitude. The causes of stimulus artifacts include actual voltage gradients between the recording electrodes, capacitive coupling between the stimulation and detection hardware, and shaping of the stimulus spike by the detection amplifier and analog filters. The magnitude of the artifacts can generally be reduced through careful hardware design, improved skin preparation, and the use of sample-and-hold amplifiers or delay circuits that exclude the stimulus from the recorded action potential trace. In general, however, the stimulus artifacts cannot be completely eliminated from peripheral evoked potential recordings and may dwarf the EP waveform even after implementing these measures.

Several methods of post-processing to remove stimulus artifacts from EP recordings have been investigated and documented. Inverse filtering to counteract the effects of the detection amplifier, fitting of an artifact to a parameterized function, estimation and subtraction of an artifact from a separate recording, a sub-threshold stimulus or a second stimulus pulse during the refractory period, and non-linear adaptive filtering techniques have all been used. While these methods have proven effective and useful, none are universally applicable and the search for new methods for stimulus artifact removal continues.

Another aspect that complicates evoked potential analysis is the compound nature of the recorded signals. Often, healthy and diseased tissues are both present and are both activated and recorded. The response of healthy tissue, having a normal amplitude and latency, can mask the effect of existing pathology. Ideally, the healthy and diseased tissues could be measured separately, but this is very difficult in practice. Alternatively, it would be useful to be able to separate the healthy and diseases responses from compound signals that contain both.

Independent component analysis (ICA) is a statistical analysis method that has applications in telecommunications, image processing, and biomedical signal analysis. ICA identifies and extracts the contributions of different, non-Gaussian sources given multiple recordings that are linear mixtures of those contributions. The mixtures may be of multiple sources of interest, in which case ICA allows tracking of the amplitude and latency of each separated source, or they may include unwanted signals such as artifacts that can, after being identified with ICA, be removed from the recordings. Often referred to as a method of blind source separation (BSS), ICA can be performed with no a-priori knowledge of the source signals other than their statistical independence, and no a-priori knowledge about the contribution of each source signal to the recorded mixtures. ICA can also be performed when limited knowledge is available or assumed about either the morphology of the source signals or their contributions to the recordings. Several ICA algorithms have been recently developed, including a fast ICA (FICA) Matlab package that is freely available on the World Wide Web.

In biomedical signal analysis, ICA has been used very promisingly in the separation of multiple sources in scalp recordings of somato-sensory, visual, or auditory evoked potentials (SEP, VEP, AEP) or for source separation and the removal of motion and eye-blink artifacts in passive electroencephalography (EEG). These applications lend themselves to ICA because they involve numerous detection electrodes recording combinations of sources from a relatively large distance. The effects of source propagation and of dissimilar filtering by the intervening tissues are neglected for this far-field recording situation and all sources are assumed to contribute an identical, but scaled, component to each recording.

This is not usually the case for peripheral EPs, which are recorded in closer proximity to a larger, more coherent group of sources. Different electrode locations over an activated muscle will produce CMAPs that differ in shape and temporal extent due to the active propagation of the generating sources and their near-field relationship to the detection electrodes. Similarly, even closely spaced detection sites along a nerve will see SNAPs that have different latencies and durations due to propagation of the sources past the electrodes and temporal dispersion among the individual action potentials that compose the compound SNAPs.

While independent component analysis (ICA) appears to be a very useful tool for blind source separation and removal of contaminating artifacts from cortical evoked potential and EEG recordings, spatially separated peripheral compound muscle and sensory nerve action potentials do not fit the model of linear mixtures normally required for ICA.

SUMMARY OF THE INVENTION

As a result, one object of the present invention is to provide a novel method for identifying constituent signal components from a plurality of evoked physiological composite signals.

And another object of the present invention is to provide novel apparatus for identifying constituent signal components from a plurality of evoked physiological composite signals.

As noted above, while independent component analysis (ICA) appears to be a very useful tool for blind source separation and removal of contaminating artifacts from cortical evoked potential and EEG recordings, spatially separated peripheral compound muscle and sensory nerve action potentials do not fit the model of linear mixtures normally required for ICA.

In accordance with the present invention, it has now been discovered that one way to overcome this problem is to record different linear mixtures of multiple sources from a single recording site. In this case, the contribution from each source is known to have an identical shape and temporal extent in all recordings. Problems associated with the propagation of near-field sources and the differences in intervening tissues, common in multiple site recordings, are eliminated. As a result, independent component analysis (ICA) can be used for blind source separation and the removal of contaminating artifacts from evoked physiological composite signals.

More particularly, the field of evoked, surface-recorded, peripheral neuromuscular electrodiagnostics involves the non-invasive activation and recording of biopotentials directly from nerve and muscle tissues. Surface-recorded, peripheral neuromuscular recordings do not lend themselves to multiple recording site ICA because the dispersive propagation of action potentials through the tissue and the "near-field" nature of the sources lead to violations of the standard assumption of signal congruency among recordings. In general, sources may be considered to be "near-field" when the spatial dimension of the physiologic activity is of the same order of magnitude as the spatial dimensions of the recording electrodes and of the spatial relationship between the electrodes and the active tissue. In accordance with the present invention, it has now been discovered that there are certain situations, however, for which multiple traces recorded from the same electrodes can be modeled as mixtures of the same, statistically independent components with different weighting coefficients—the same model that has been used to apply ICA to traces from multiple recording sites. The use of multiple signals from a single sensor obviates the assumption that different sources contribute similar components to each recording but requires a means, other than spatial separation, to generate multiple and different mixtures of the same signal components.

In one preferred form of the invention, multiple and different mixtures of the same signal components (i.e., a plurality of evoked physiological composite signals) are generated by successively activating the patient's tissue with different stimuli. And in one particularly preferred form of the invention, the composite signals are generated by applying different levels, or grades, of the same stimuli to the tissue. Such stimuli may comprise electrical stimuli, mechanical stimuli, magnetic stimuli, etc.; electrical stimuli is generally most preferred.

The present invention can be described as single channel independent component analysis (SCICA). SCICA is a technique that allows ICA to be applied to peripheral evoked potential (PEP) signals. Applications of SCICA to peripheral electrodiagnostics include the removal of stimulation artifacts and the deconvolution of overlapping components. Removal of corrupting artifacts can improve the accuracy of electrodiagnostic parameter estimation. Removal of corrupting artifacts also permits improved diagnostic indices to be identified in the independent component domain, which may more closely represent the underlying electrophysiology. SCICA may also be implemented within a fully automated expert system performing waveform analysis for peripheral neuromuscular diagnostics.

BRIEF DESCRIPTION OF THE DRAWINGS

These and other objects and features of the present invention will be more fully disclosed or rendered obvious by the following detailed description of the preferred embodiments of the invention, which is to be considered together with accompanying drawings wherein like numbers refer to like parts and further wherein.

DETAILED DESCRIPTION OF THE PREFERRED EMBODIMENTS

Independent Component Analysis

A linear mixture model assumes that n linear mixtures, $x_1, x_2, \ldots, x_n$, of n sources, $s_1, s_2, \ldots, s_n$, are recorded. The resulting signals can each be written as $$x_j = a_{j1}s_1 + a_{j2}s_2 + \ldots + a_{jn}s_n, \text{ for } j=1, 2, 3, \ldots, n. \tag{1}$$

Each mixing coefficient, $a_{jk}$, defines the amount of component $s_k$ that is present in recorded signal $x_j$. While there is no explicit time reference, both the recorded mixtures and the independent sources may be thought of as multiple (time) samples of a random variable. In matrix notation the model can be written as $$x = As \tag{2}$$

where A is the mixing matrix. Both the source components and the mixing matrix are completely unknown. Estimation and extraction of these elements from the recorded signals constitutes blind source separation. Once the (square) mixing matrix has been estimated, its inverse can be calculated and used to extract the source components. This is expressed as $$s = A^{-1}x = Wx. \tag{3}$$

Independent component analysis (ICA) relies upon the statistical independence of the source variables, and the fact that they are each distributed in a non-Gaussian manner, to perform blind source separation. Central limit theorems suggest that mixtures of non-Gaussian variables will be distributed in a more Gaussian manner than their components. ICA determines independent components, therefore, by finding directions, in the n-dimensional sample space, for which the Gaussian nature of the marginal (projected) probability density function is minimized. The components of the un-mixing matrix, W, are defined by these directions. While the concept is relatively straightforward, there is wide variation in both the way that "Gaussian-ity" is measured and the manner with which the minimization routine is performed.

For this work, a freely available FastICA package for MATLAB (Mathworks, Inc., Natick, Mass.) may be used. FastICA uses a fixed-point iteration algorithm to solve the ICA problem in a rapid and robust manner. The FastICA algorithm is run using random vectors to initialize the IC solutions and a hyperbolic-tangent non-linearity within the optimization routine.

Sensory Nerve Action Potentials

The electrically evoked, surface recorded compound sensory nerve action potential (SNAP) is a superposition of components arising from both the underlying biophysical interactions (signal) and directly from the application of an external stimulus pulse (artifact). In sensory nerve recordings the basic signal components are single fiber action potentials (SFAPs) and each recorded SNAP is potentially composed of tens of thousands of SFAPs. Single fiber potentials are too small to be detected individually on the surface of the skin due to the physical limitations of modern instrumentation, and it is only through superposition of SFAPs that the SNAP can be recorded. Due to the large number of fibers, the distribution of fiber size and position within the nerve is nearly a continuum and it is therefore quite common to consider populations of fibers, rather than individual fibers, to be the basic unit of excitation. Given this consideration, the contribution from a population of fibers will change in a graded fashion depending on the number of fibers in that population that are activated by a particular stimulus.

The relationship between the stimulus and the resulting signal is known as the stimulus response curve (SRC). In general, as the stimulus increases in either amplitude or duration the size of the response also increases. For sensory signals this amounts to an increased contribution from one or more fiber populations. The SRC for a SNAP is typically a sigmoid with no response for very small stimuli, a saturated or maximal response to large stimuli, and monotonically increasing response magnitude in between those two extremes.

SNAP recordings often include artifact components associated with the method of nerve stimulation. Such artifacts are primarily in the region of the stimulus itself but frequently have components lasting many milliseconds, corrupting the action potential signal. The stimulus artifact can have multiple components that come about from the different artifact generating processes. Each component can have not only a different temporal extent, but also its own SRC. Stimulus artifact response curves are believed to be strongly correlated with the stimulus amplitude, duration, or the product of the two (intensity).

An electrically evoked, surface recorded compound action potential, C, can be modeled as the sum of signal and artifact components, $$C(j, t) = \sum_{m=1}^{M} p_m(j)\phi_m(t) + \sum_{n=1}^{N} q_n(j)\gamma_n(t). \quad (4)$$

where
M is the total number of basis sources (SFAP populations) that potentially contribute to the compound signal,
$\phi_m$ is the $m^{th}$ basis source waveform,
$P_m$ is a coefficient reflecting the amplitude dependence of $\phi_m$ on the stimulus used to evoke C,
N is the total number of artifact components that potentially contribute to the signal,
$\gamma_n$ is the form of the $n^{th}$ basis artifact component,
$q_n$ is a coefficient reflecting the amplitude dependence of $\gamma_n$ on the stimulus used to evoke C,
t is an independent variable representing time, and
j is an independent variable reflecting the intensity of the applied stimulus pulse—analogous to j in Equation 1.

Sources and mixtures are considered to be random variables for the purposes of ICA so the implicit time dependence can be dropped if each time sample of the mixture is considered to be a single realization of the underlying random variable. In this case, the recorded signal can be rewritten as $$C = \sum_{m=1}^{M} p_m \phi_m + \sum_{n=1}^{N} q_n \gamma_n \quad (5)$$

In matrix form this equation becomes $$c = P\phi + Q\gamma \quad (6)$$

where c is a random column vector whose elements are the L different mixtures, P is an L×M matrix of mixing coefficients for the individual signal components, $\phi$ is a column vector of M independent signal components, Q is an L×N mixing-matrix specific to the contribution of artifact components, and $\gamma$ is a column vector of the N independent artifact components. This mathematical structure can be concatenated to yield $$c = [P \ Q] \begin{bmatrix} \varphi \\ \gamma \end{bmatrix} = As. \quad (7)$$

In this final formulation, A is an overall mixing-matrix containing L×(M+N) coefficients of mixing for both the source and artifact components and s is a vector of source and artifact components. The variables A and s are used in Equation 7 to point out the similarity between this formulation of a SNAP recording and the ICA model of Equations 2 and 3.

Figure 1:
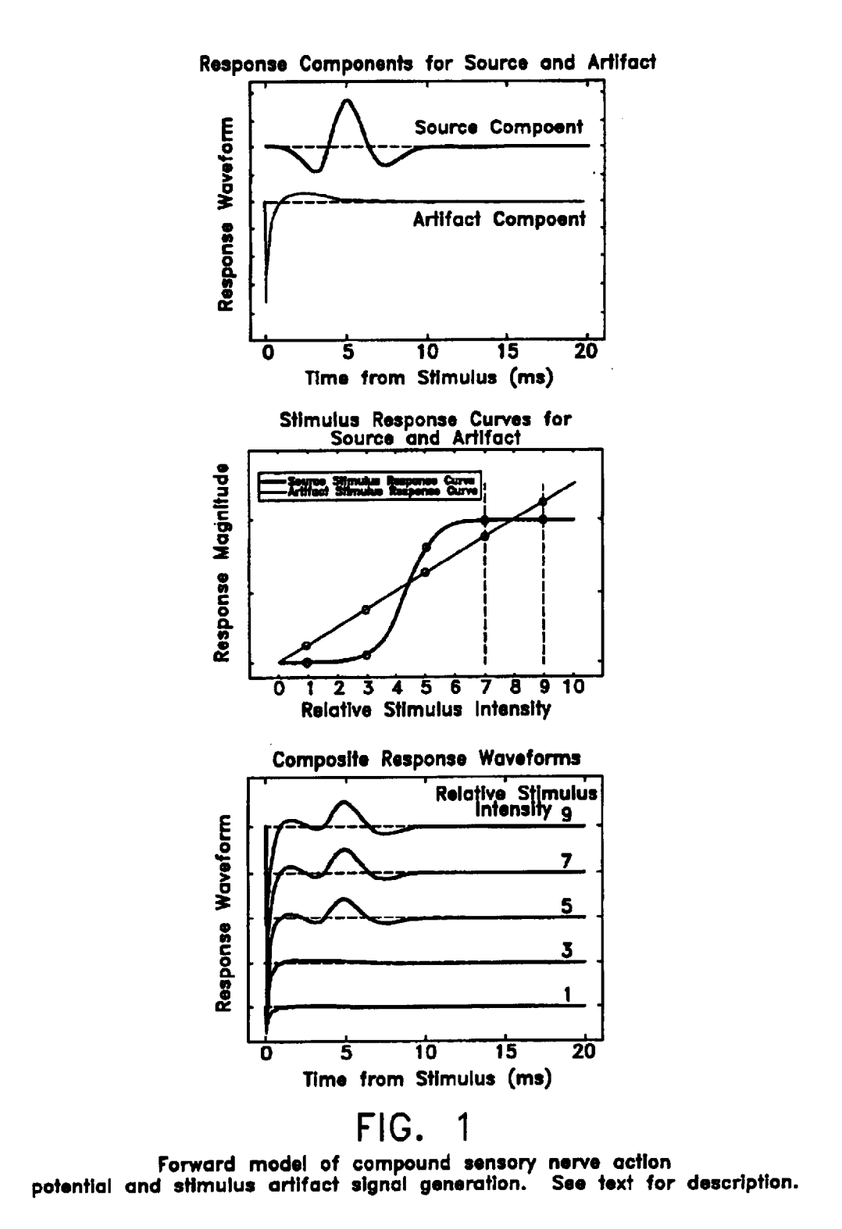
FIG. 1 is a multi-panel schematic view illustrating a forward model of compound sensory nerve action potential and stimulus artifact signal generation.

This forward model of sensory nerve compound action potential generation is illustrated in FIG. 1 for the simple case of a single source component and a single artifact component. The top panel shows both components as time series plotted with normalized variance. The black trace is a simulated action potential and the gray trace is a simulated stimulus artifact. At each time sample these two waveforms define the component vector, s in Equation 7. The center panel of FIG. 1 shows simulated SRCs for each of the signal components. Relative stimulus strength is plotted along the x-axis and response magnitude along the y-axis. Again, the source SRC is plotted in black and the artifact SRC in gray. These curves represent the mixing matrix, A, for this simple example. Circular markers indicate the relative response magnitude for five different stimulus levels. Stimulation at each of these levels will evoke compound signals that are a superposition of the source and artifact components, each scaled by the values of their own SRC. The bottom panel shows the simulated compound signals that result from stimulation at the indicated levels.

The model of an electrically evoked, surface recorded, peripheral compound action potential developed above and illustrated in FIG. 1 fits precisely the signal model required for the application of independent component analysis. Instead of using multiple recording sites to generate differing mixtures, this approach uses a single recording site and activates the nerve with different stimuli in order to generate the different mixtures (i.e., the plurality of evoked physiological composite signals needed for the analysis). The assumption made in ICA that each source has a congruent contribution to all mixtures is trivialized through the use of a single electrode pair. It is replaced, however, by a requirement that signal components scale, linearly or non-linearly, with changes in stimulus intensity but do not alter their form. When this requirement is met, source and artifact components of the signals recorded from a single electrode site may be separated through independent components analysis.

Single-Channel ICA

Assuming the above model, single-channel independent component analysis (SCICA) can be used for the identification and removal of stimulus artifacts from compound SNAP recordings. Different mixtures of signal and artifact are recorded at a single site by varying the intensity of the activating stimulus. Disparities in the way that signal and artifact sources respond to various stimuli produce an ensemble of mixtures and allow SCICA to separate the artifact components from the action potential components of interest.

Figure 2:
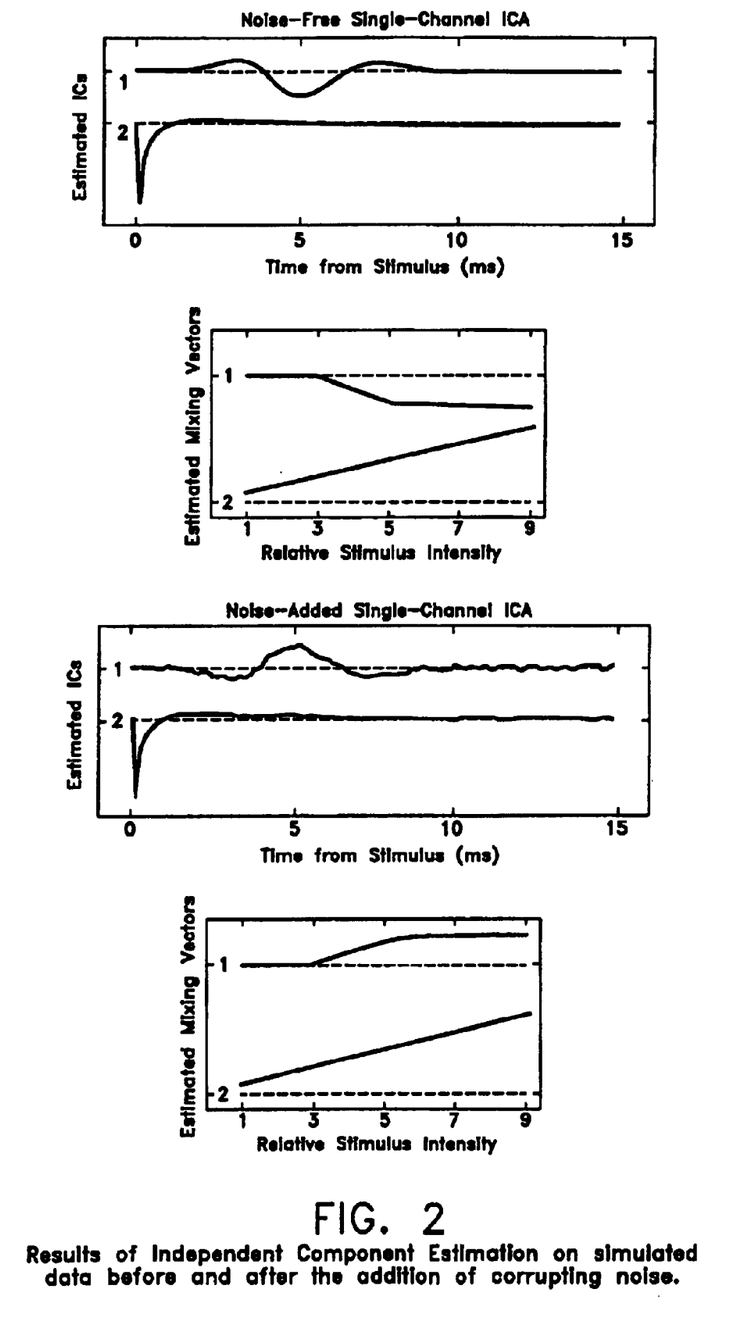
FIG. 2 is a multi-panel schematic view illustrating the results of Independent Component Estimation on simulated data before and after the addition of corrupting noise.

FIG. 2 shows the use of SCICA to estimate the two signal components from the example of FIG. 1. The FastICA algorithm was applied to the composite data in the bottom panel of FIG. 1 before and after adding corrupting noise to the signals. The top two panels of FIG. 2 show the results of ICA estimation without corrupting noise and the bottom two graphs were generated from noise-added data. Two estimated independent components and their associated mixing vectors (contribution to the original data) are shown. Both sets of results demonstrate estimation of the two original signal components. The fact that the first IC in the top panel and its mixing vector are inverted illustrates the polarity invariance of the IC algorithm. In the case of noisy data, both IC estimates are corrupted but their general shape, and hence the magnitude of their mixing vectors, remains unchanged.

Figure 3:
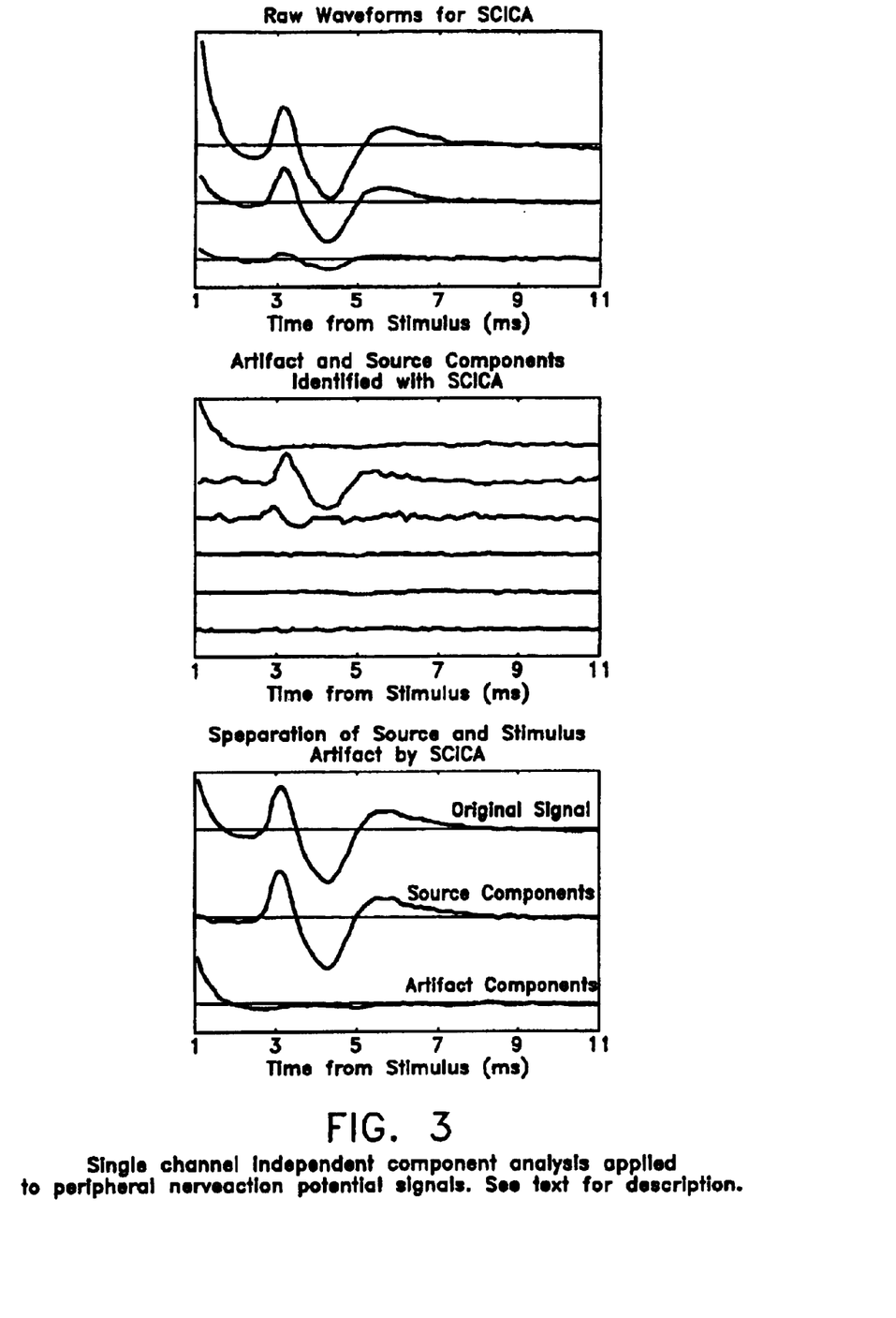
FIG. 3 is a multi-panel schematic view illustrating single channel independent component analysis applied to experimentally recorded peripheral nerve action potential signals.

The single-channel ICA technique can also be applied to experimentally recorded compound action potential data for artifact removal. An example of this is shown in FIG. 3. The top panel shows single-channel sensory nerve action potential data recorded from a human subject's middle finger following electrical activation at the wrist. The three traces were activated with different magnitude stimuli and are, therefore, different mixtures of stimulus artifact (the initial decaying signal) and action potential (starting at approximately 2.8 ms) components.

Applying ICA to such data results in the identification of the independent components (ICs), shown in the second panel. Each of the ICs is scaled to represent its contribution to a single trace of the ensemble. The top trace is the first IC returned and its shape clearly associates it with the stimulus artifact. The next two ICs demonstrate characteristics of the action potential source, while the remaining components are mainly noise with minimal contributions to the original signal. The bottom graph shows three reconstructions of data using the estimated ICs. The top reconstruction uses all 6 ICs. The center trace excludes the first (artifact) IC from the sum while the bottom trace is generated from only the artifact IC. This graph clearly shows the ability of SCICA to separate signal and artifact components. The artifact-removed (center) trace is generally highly desirable inasmuch as it yields more accurate measurement of action potential parameters and hence permits more accurate assessment of tissue function.

Automated SCICA

The use of ICA within an expert or automated system presents several issues of implementation. Among these are the determination that acquired data is of sufficient quality and fidelity to expect accurate IC estimation, the selection of appropriate data dimension prior to ICA and the appropriate number of ICs to return from the analysis, and selection of algorithm parameters and IC estimate initializations to maximize the probability of convergence on an appropriate solution. These issues apply to any automated application of ICA and must be properly understood before ICA can be an effective tool independent of a human operator.

The data of FIG. 3 illustrates an important aspect, specific to artifact removal, which further affects ICAs potential utility when applied within an expert system. Independent components are returned in an unspecified order, with ambiguities in polarity and amplitude. In the reconstruction step, source and artifact ICs must be identified and segregated. The inherent ambiguities of the technique make automated reconstruction a challenge.

In the example, a human expert identified the first IC as being an artifact component due to the characteristic shape of its time series. Attempts might be made to duplicate this type of reasoning process using artificial neural networks trained to discriminate between artifact and source base on time or frequency domain qualities. This approach would require a substantial developmental dataset for training of the neural network and would assume that the dataset encompassed all possible characteristics of interest. The single-channel ICA model developed for peripheral evoked potentials provides another potentially useful method of automating the identification of source and artifact components. This method, motivated by the center panel of FIG. 1, is based on the coefficients of mixing returned by ICA. The vertical dotted lines in that plot point out two stimulus levels between which the source contribution changes very little but the artifact contribution continues to grow. This region of plateau in the action potential SRC corresponds to maximal or supramaximal activation of the nerve. Increasing the stimulus magnitude can no longer increase the action potential response because the stimulus is already of sufficient magnitude to activate all of the large nerve fibers (which are the contributors to the recorded sensory nerve action potential). This behavior is also believed to be reflected in the mixing vectors so that, as the stimulus magnitude is increased beyond the maximal level, mixing coefficients of artifact ICs will continue to grow while those of source components stabilize.

Figure 4:
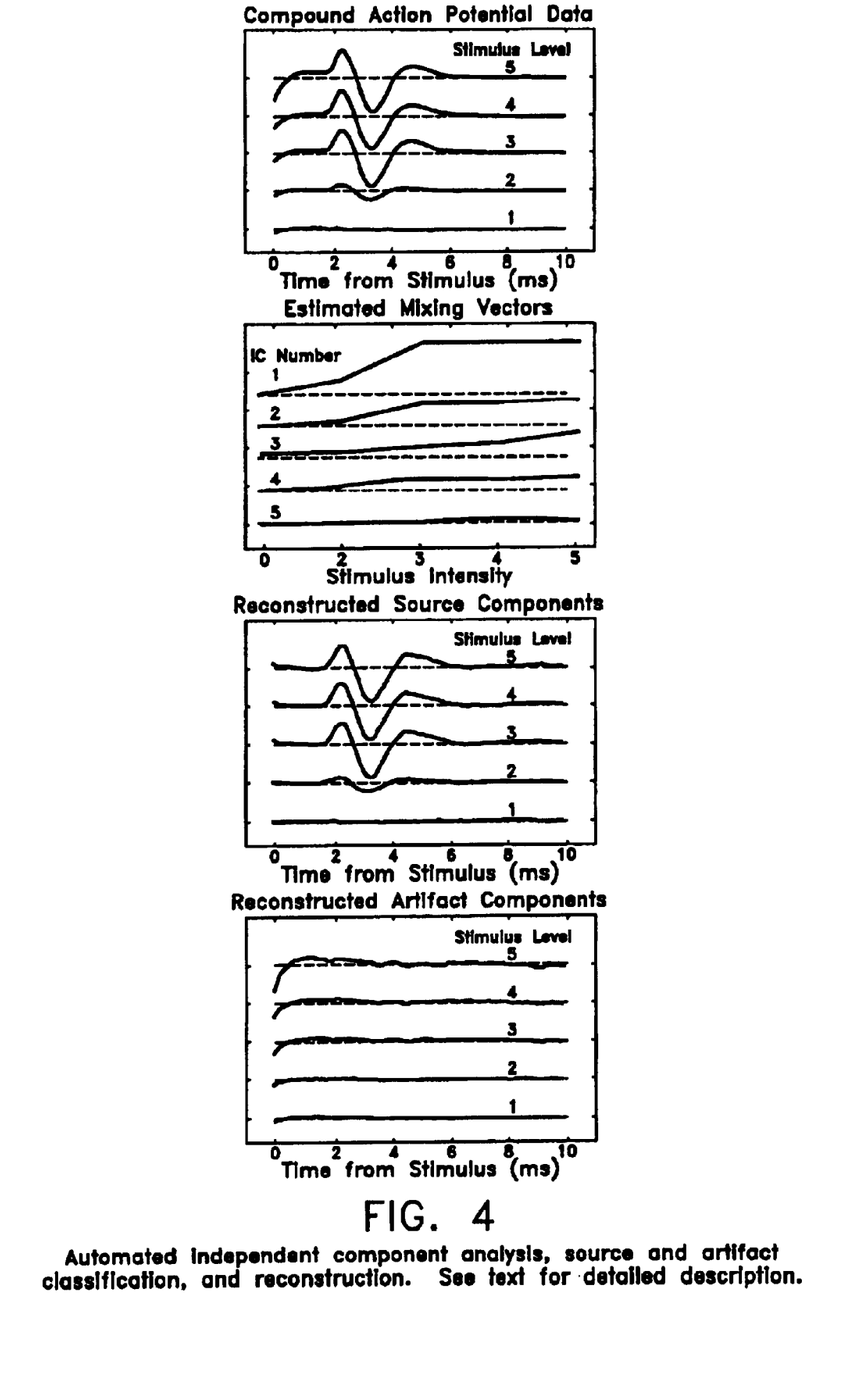
FIG. 4 is a multi-panel schematic view illustrating the use of single channel independent component analysis to perform source and artifact classification, and reconstruction of experimentally recorded peripheral nerve action potential signals.

Application of this method to experimental action potential recordings is demonstrated in FIG. 4. The uppermost panel shows a series of five compound action potential waveforms activated by five different intensity stimuli. Each trace in this plot is an average of twelve individual recordings. The magnitude of the physiological source component clearly grows through the first three stimulus levels, but appears to be maximal (stable) for the last three. These action potential data were input to the FastICA algorithm and five independent components were returned. The mixing vectors for those five ICs are shown in the next plot (i.e., the second panel of FIG. 4). The x-axis corresponds to the five different stimulus intensities used for data acquisition and the value of each vector (its difference from the dotted line) indicates that IC's contribution to the signal at that stimulus level. The plateau effect of reaching a maximal stimulus level is apparent in the first IC mixing vector. Between the fourth and fifth stimuli, the percent change in that vector is quite small. The contribution of the second and third ICs, on the other hand, changes significantly between the fourth and fifth stimuli—indicating that those ICs are closely associated with the artifact component. This measure of association can be used to automatically separate source and artifact ICs.

The bottom two panels of FIG. 4 show reconstructed source and artifact estimates following automated independent component analysis. The percent change in each independent component's contribution between the last two stimuli was used to classify each component as either source-like or artifact-like. The reconstructed waveforms demonstrate effective removal of stimulus artifacts from the compound signals. The ability to perform automated reconstruction in this way relies on stimulation at and above the maximal level for the SNAP components.

EXAMPLE

Figure 5:
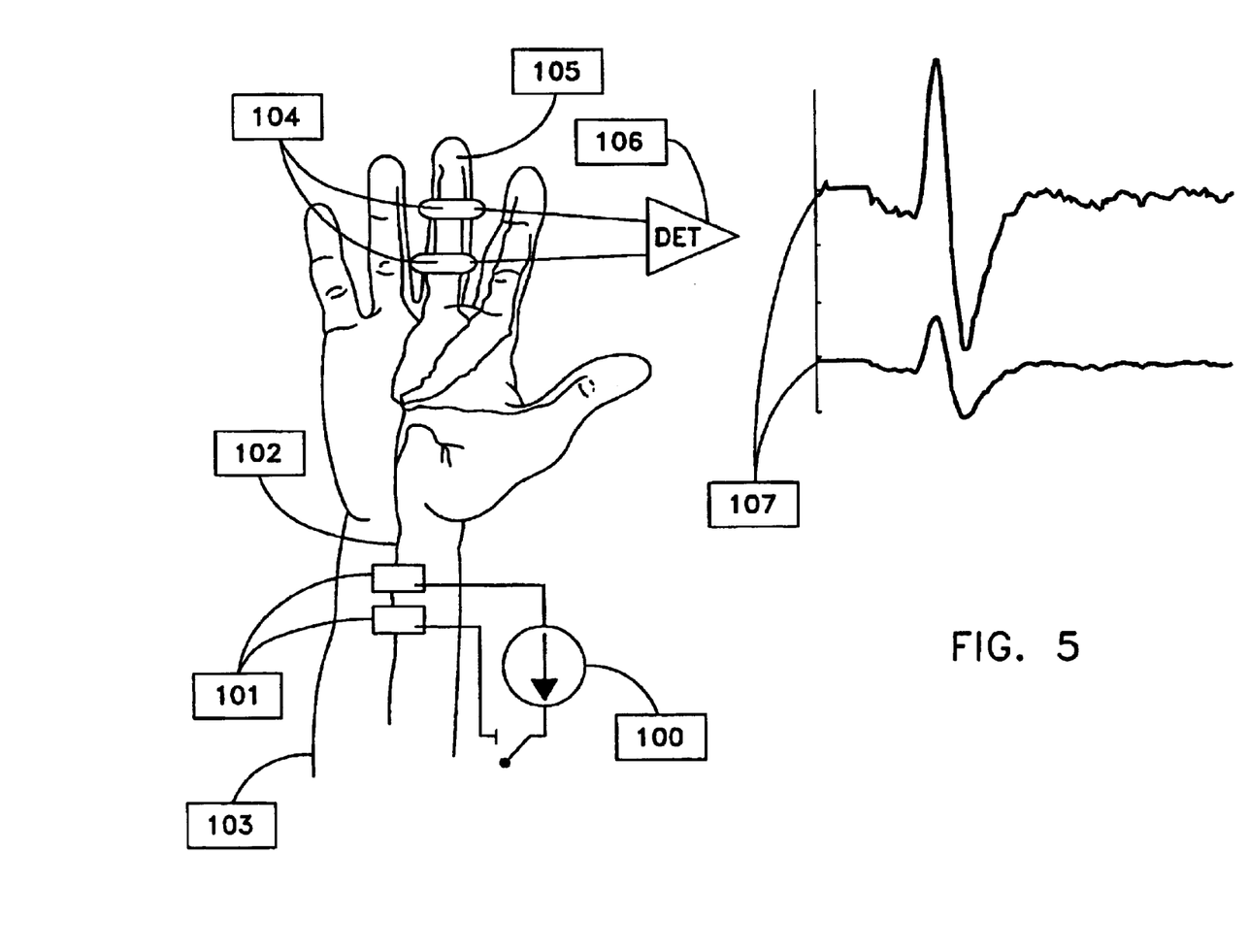
FIG. 5 is a schematic view illustrating one preferred mode of implementing the present invention.

The preferred embodiment of the present invention provides for the estimation of constituent components of multiple, electrically evoked, peripheral sensory nerve signals. FIG. 5 illustrates this embodiment. A variable electric current source 100 is connected to a pair of skin surface stimulation electrodes 101 in such a way that pulsed electrical current stimuli can be delivered to a human subject's median nerve 102 through the surface of the subject's arm 103. Multiple stimuli, of different stimulus magnitudes, are delivered to the nerve. Each stimulus evokes a compound nerve action potential that travels distally along the median nerve toward the subject's finger 105. Evoked compound nerve potentials activated in this manner consist of a combination of individual action potentials from multiple nerve fiber sub-populations, each having their own unique bioelectrical characteristics. Varying the magnitude of stimulation results in evoked compound potentials consisting of different mixtures of these same constituent components. Multiple action potentials, resulting from the different magnitude stimuli, are recorded at a detection site by a system consisting of detection electrodes 104 and detection circuitry 106. The recorded compound nerve action potentials 107 consist of different combinations of the same constituent components. A method of mathematical blind source separation, such as independent component analysis, is used to identify the underlying constituent components within the recorded compound potentials. In addition to the underlying components, the amount that each component contributes to the recorded signals can be estimated by the same technique.

More particularly, surface recordings of electrically evoked compound action potentials are preferably made using an NC-stat™ Nerve Conduction Monitoring System (Neurometrix, Inc., Waltham, Mass.) modified to acquire both motor responses (CMAPs) and sensory potentials (SNAPs). The battery-powered NC-stat is a handheld device that both activates, using constant current stimuli, and records neuromuscular responses. For motor signal recording, the NC-stat uses an analog band-pass filter with cutoffs at 1.5 Hz and 3.1 kHz. The gain of the device is variable, with a minimum gain of 55 dB and a maximum of 120 dB. The gain is adjusted automatically for CMAP acquisition in order to make efficient use of the available dynamic range. As part of a standard nerve conduction test, the NC-stat applies a series of ramped stimuli that increase in intensity and maps the magnitude of the response to those stimuli.

The modified device allows for SNAP acquisition by switching the high-pass filter components to produce a pass-band from 160 Hz to 3.1 kHz. SNAPs are acquired, following a series of ramped stimuli, with a fixed gain of 91.4 dB. The modified device also allows for storage of CMAP and SNAP responses to ramped data. The stored waveforms are preferably downloaded to a PC for post-processing and viewing.

Motor responses are recorded non-invasively from the hypothenar muscle of the hand following stimulation at the wrist. Both the stimulation and detection electrodes are part of a NC-stat Median Biosensor™ (Neurometrix, Inc., Waltham, Mass.), which is an integrated Ag/AgCl sensor array fabricated on a flexible substrate. The biosensor is placed on the wrist following preparation of the skin with an alcohol and pumice electrode preparation pad (Professional Disposables, Inc., Orangeburg, N.Y., Cat. No. B59800). When the biosensor is in place, the stimulating cathode is located approximately 3 cm from the distal wrist crease on the ventral portion of the wrist, directly over the median nerve. The differential detection electrodes are also located proximal to the hand on the medial and lateral surfaces of the wrist. The reference electrode is located directly distal to the stimulating cathode very close to the wrist crease.

Antidromic median nerve sensory responses are recorded from ring electrodes around the third digit. The proximal detection electrode is located at the first interphalangeal joint and the second detection electrode is 2.5 to 3 cm distal to that site. The stimulating electrodes and the detection reference electrode on the NC-stat Median Biosensor are used in the same capacity for sensory signal acquisition. The NC-stat can deliver current-controlled, square-wave stimuli with a driving voltage of up to 200 V. The ramped stimuli are preferably delivered in a progression intended to generate a monotonically increasing response from the nerve. In addition, the ramped stimuli are preferably delivered so that at least the smallest stimulus, and in some cases the smallest 2 or 3 stimuli, will be sub-threshold and produce no discernable motor or sensory response.

During the stimulus itself, and for 1.5 ms following stimulus onset, the input electronics are shunted to avoid saturation of the amplifiers by the stimulus pulse and to reduce the amplitude and duration of stimulus artifacts. Data is acquired at a rate of 10 kHz for 12.8 ms beginning at the onset of the stimulus. The acquired data is digitized with 10-bit precision over a 10 V dynamic range.

The acquired data is analyzed using independent component analysis (ICA), preferably using a freely available FastICA package for MATLAB. FastICA uses a fixed-point iteration algorithm to solve the ICA problem in a rapid and robust manner. Principle components analysis is used to reduce the data dimension. Data dimensions from 1 to 6 were investigated. The number of estimated ICs was always equal to the reduced dimension of the data. The FastICA algorithm was run using random vectors to initialize the IC solutions and a hyperbolic-tangent non-linearity within the optimization routine. A maximum of 2500 iterations were allowed for the algorithm to converge to each IC solution. If the algorithm failed to converge, up to two additional solution attempts were made with re-initialized IC solutions.

CONCLUSION

As noted above, surface recorded peripheral nerve signals do not lend themselves to effective analysis by traditional, multi-channel independent components due to the difficulty in recording the same signal at different sites. In accordance with the present invention, a new method has been described and demonstrated, however, that does allow ICA to be utilized on these data. This new method uses different evoking stimuli to produce different mixtures of source and artifact components that can be recorded from a single site. The resulting plurality of evoked physiological composite signals can then be processed using a blind source separation technique (for example, by single-channel independent component analysis) to identify the underlying constituent components within the recorded composite signals and to identify the amount that each component contributes to a composite signal. As a result, signal-contaminating artifacts may be removed from the evoked physiological composite signals, thereby permitting more accurate assessment of tissue function.

It should also be appreciated that the present invention may be practiced using other blind source separation techniques. By way of example but not limitation, it is believed that the present invention may be practiced using blind source separation techniques such as artificial neural networks, Bayesian blind source separation, Time-Frequency Based Blind Source Separation, Blind Source Separation by Sparse Decomposition, Frequency Domain Blind Source Separation, Blind Source Separation Based on the Characteristic Function, etc.

In addition to the foregoing, it should also be appreciated that the invention may be practiced in plural form so as to improve the accuracy of identifying the constituent signal components. More particularly, in this form of the invention, activation is effected so as to generate at least two distinct composite signals, the composite signals can be recorded at a first anatomical site X, and those recordings processed so as to identify the constituent signal components; and activation is effected so as to generate at least two distinct composite signals, the composite signals can be recorded at a second anatomical site Y, and those recordings processed so as to identify the constituent signal components; and then the results of these two independent derivations may be further processed, in ways well known in the art of signal processing, so as to improve the accuracy of identifying the constituent signal components. If desired, the responses recorded at the two anatomical sites may result from the same activation event.

Or it is possible to generate at least two distinct composite signals, record those composite signals at at least two separate anatomical sites, and then process the recorded signals, collectively, using blind source separation techniques so as to determine the constituent signal components.

What is claimed is:

1. A method for identifying constituent signal components from a plurality of evoked physiological composite signals, said method comprising:

activating a subject's anatomy so as to generate the plurality of composite signals, wherein at least two of said composite signals comprise distinct mixtures of the same constituent signal components;

recording, at a single anatomical site, the composite signals; and performing blind source separation on the composite signals so as to identify the constituent signal components.

2. A method according to claim 1 wherein said blind source separation is performed so as to identify the amount that each constituent signal component contributes to the composite signals.

3. A method according to claim 1 wherein said blind source separation is performed using independent component analysis.

4. A method according to claim 1 wherein at least one of the constituent signal components is an evoked neuromuscular response.

5. A method according to claim 4 wherein the evoked neuromuscular response is a compound muscle action potential (CMAP).

6. A method according to claim 4 wherein the evoked neuromuscular response is a sensory nerve action potential (SNAP).

7. A method according to claim 1 wherein at lease one of the constituent signal components is a directly recorded artifact of activating a subject's anatomy.

8. A method according to claim 1 wherein activating a subject's anatomy involves activating neuromuscular tissue.

9. A method according to claim 8 wherein the neuromuscular tissue comprises a peripheral nerve.

10. A method according to claim 1 wherein a subject's anatomy is activated with different levels of the same type of stimuli.

11. A method according to claim 10 wherein the stimuli comprises electrical stimuli.

12. A method according to claim 10 wherein the stimuli comprises mechanical stimuli.

13. A method according to claim 10 wherein the stimuli comprises magnetic stimuli.

14. A method according to claim 1 wherein the method comprises the additional step of removing a constituent signal component from a composite signal so as to yield a calculated composite signal.

15. A method according to claim 14 wherein the removed constituent signal component comprises a directly recorded artifact of activating the subject's anatomy.

16. A method according to claim 1 wherein the method comprises the additional step of removing a plurality of constituent signal components from a composite signal so as to yield a calculated composite signal.

17. A method according to claim 1 wherein the method comprises the additional step of constructing a calculated composite signal from at least one of the identified constituent signal components.

18. A method according to claim 17 wherein said calculated composite signal reduces the contribution of directly recorded artifacts of activating the subject's anatomy vis-à-vis the original composite signal.

19. A method according to claim 1 wherein the method comprises the additional step of relating the identified signal components to their underlying phenomena.

20. A method according to claim 19 wherein the underlying phenomena is anatomical function.

21. A method according to claim 19 wherein the underlying phenomena is an artifact of activating the subject's anatomy.

22. A method according to claim 1 wherein the blind source separation is performed so as to separate out several constituent signal components, each of which results from anatomical function.

23. Apparatus for identifying constituent signal components from a plurality of evoked physiological composite signals, said apparatus comprising:

activating means for activating a subject's anatomy so as to generate the plurality of composite signals, wherein at least two of said composite signals comprise distinct mixtures of the same constituent signal components;

recording means for recording, at a single anatomical site, the composite signals; and separation means for performing blind source separation on the composite signals so as to identify the constituent signal components.

24. Apparatus according to claim 23 wherein said separation means are adapted to identify the amount that each constituent signal component contributes to the composite signals.

25. Apparatus according to claim 23 wherein said separation means are adapted to use independent component analysis.

26. Apparatus according to claim 23 wherein at least one of the constituent signal components is an evoked neuromuscular response.

27. Apparatus according to claim 26 wherein the evoked neuromuscular response is a compound muscle action potential (CMAP).

28. Apparatus according to claim 26 wherein the evoked neuromuscular response is a sensory nerve action potential (SNAP).

29. Apparatus according to claim 23 wherein at lease one of the constituent signal components is a directly recorded artifact of activating the subject's anatomy.

30. Apparatus according to claim 23 wherein said activating means are adapted to activate neuromuscular tissue.

31. Apparatus according to claim 30 wherein the neuromuscular tissue comprises a peripheral nerve.

32. Apparatus according to claim 23 wherein said activating means are adapted to activate the subject's anatomy with different levels of the same type of stimuli.

33. Apparatus according to claim 32 wherein the stimuli comprises electrical stimuli.

34. Apparatus according to claim 32 wherein the stimuli comprises mechanical stimuli.

35. Apparatus according to claim 32 wherein the stimuli comprises magnetic stimuli.

36. Apparatus according to claim 23 wherein the apparatus comprises removal means for removing a constituent signal component from a composite signal so as to yield a calculated composite signal.

37. Apparatus according to claim 36 wherein the removed constituent signal component comprises a directly recorded artifact of activating the subject's anatomy.

38. Apparatus according to claim 23 wherein the apparatus comprises removal means for removing a plurality of constituent signal components from a composite signal so as to yield a calculated composite signal.

39. Apparatus according to claim 23 wherein the apparatus comprises reconstruction means for constructing a calculated composite signal from at least one of the identified constituent signal components.

40. Apparatus according to claim 39 wherein said calculated composite signal reduces the contribution of directly recorded artifacts of activating the subject's anatomy vis-a-vis the original composite signals.

41. Apparatus according to claim 23 wherein the apparatus comprises relating means for relating the identified signal components to their underlying phenomena.

42. Apparatus according to claim 41 wherein said relating means comprises a discrimination algorithm running on a computer.

43. Apparatus according to claim 41 wherein the underlying phenomena is anatomical function.

44. Apparatus according to claim 41 wherein the underlying phenomena is an artifact of activating the subject's anatomy.

45. Apparatus according to claim 23 wherein the blind source separation is performed so as to separate out several constituent signal components, each of which results from anatomical function.

46. A method for identifying constituent signal components from a plurality of evoked physiological composite signals, said method comprising:

activating a subject's anatomy so as to generate the plurality of composite signals, wherein at least two of said composite signals comprise distinct mixtures of the same constituent signal components;

recording, at a single anatomical site, the composite signals; and processing the composite signals so as to identify the constituent signal components.

47. Apparatus for identifying constituent signal components from a plurality of evoked physiological composite signals, said apparatus comprising:

activating means for activating a subject's anatomy so as to generate the plurality of composite signals, wherein at least two of said composite signals comprise distinct mixtures of the same constituent signal components;

recording means for recording, at a single anatomical site, the composite signals; and processing the composite signals so as to identify the constituent signal components.

48. A method according to claim 1 wherein the subject's anatomy is activated at at least two separate anatomical sites.

49. A method according to claim 23 wherein said activating means activate the subject's anatomy at at least two separate anatomical sites.

* * * * *